United States Patent

Krumeich et al.

[11] Patent Number: 5,417,117
[45] Date of Patent: May 23, 1995

[54] PROCEDURE AND APPARATUS FOR DETERMINING THE VULCANIZATION COEFFICIENT OF ELASTOMERS

[75] Inventors: Peter Krumeich, Stuttgart-Feuerbach; Gerhard Streit, Flein; Hans Fuchs, München; Christian Strauss, Dachau, all of Germany

[73] Assignee: Parker-Pradifa GmbH, Bietigheim-Bissingen, Germany

[21] Appl. No.: 855,811

[22] Filed: Mar. 23, 1992

[30] Foreign Application Priority Data

Mar. 23, 1991 [DE] Germany ............... 41 09 696.7

[51] Int. Cl.⁶ .................................... G01N 11/00
[52] U.S. Cl. ........................................... 73/823
[58] Field of Search ............. 73/800, 818, 822, 823, 73/825

[56] References Cited

U.S. PATENT DOCUMENTS

| | | | |
|---|---|---|---|
| 4,238,952 | 12/1980 | Koopermann et al. | 73/822 |
| 4,633,718 | 1/1987 | van Engelshoven | 73/822 |
| 5,065,331 | 11/1991 | Vachon et al. | 73/800 |

FOREIGN PATENT DOCUMENTS 0459896 12/1991 European Pat. Off. ....... 73/822

Primary Examiner—Robert Raevis
Attorney, Agent, or Firm—Christopher H. Morgan

[57] ABSTRACT

The object of the invention is a procedure for vulcanization which includes a determination of the vulcanization coefficient of an elastomeric workpiece, and an apparatus for the application of the procedure. Prior art is the measurement of the rapture strength or the penetration depth of a needle and the calculation of the vulcanization coefficient from the measured value. The disadvantage is its restriction to the application for time-consuming measurements of samples taken at not too short intervals. Series testing is excluded. The task consists in defining a procedure which leaves the workpiece undestroyed and where the measuring time is so short that it can be applied in series; and in the development of the appropriate apparatus. The solution is a procedure where the workpiece to be tested is compressed and suddenly relieved, whereupon the recovery distance is followed and an asymptotic value determined from it, from which, after obtaining the result of the determination of the known vulcanization coefficient of at least two comparison specimens, the vulcanization coefficient of the workpiece can be determined graphically or by way of calculation; as well as an apparatus with a laser element for spreading, collimating and focussing a parallel beam of light, the light spot of which on the specimen surface is examined optoelectronically and maintained constant by way of the readjustment of the objective, while at the same time the recovery distance is measured; in particular using a workpiece adjusting device 10, a compressing device 12, a distance/time measuring device 14, and an electronic evaluation unit 16 with an electronic application system 18.

5 Claims, 2 Drawing Sheets

PROCEDURE AND APPARATUS FOR DETERMINING THE VULCANIZATION COEFFICIENT OF ELASTOMERS

The invention relates to a procedure for determining the vulcanization coefficient of a principally plane-parallel, elastomeric material testing specimen of a finished part or the part itself; as well as an apparatus for carrying out the procedure. The determination of the vulcanization coefficient serves mainly for the verification of a complete vulcanization, p.e. of seals manufactured in series.

In the known random-specimen procedure a specimen of the material is subjected to the measurement of either the rupture strength or the penetration depth of a needle, which both enable the determination of the vulcanization coefficient. These two known procedures are obviously not suitable for series testing of the vulcanization coefficient because in the first case, the workpiece is destroyed and in the second case, like in the first one, the determination does not keep pace with the manufacturing cycle. The invention is based on the knowledge that between the vulcanization coefficient of a workpiece to be determined, on the one hand, and its behavior after a compression of the workpiece, on the other hand, there is a verifiable correlation following a set pattern. The invention is based on the task of defining a procedure for determining the vulcanization coefficient of an elastomeric material specimen of a finished part or of the part itself, which leaves the workpiece undestroyed and where the time required for the determination is so short that it can be applied in series.

According to the invention the task is solved in such a way that the material specimen and/or the finished part is compressed, held, during a setting time, under a possibly constant pressure, and then suddenly relieved, whereupon the retardation of the relieved, possibly plane, surface of the specimen is measured.

The covered recovery distance (S) of a selected point of the relieved specimen surface, or any of its derivations (recovery speed and/or acceleration) as a function of time (t) is measured so long till the asymptotic value ($S_\infty$) of the recovery distance (S) can be determined for an infinitely long measuring time; and this asymptotic value ($S_\infty$) is determined by means of the equation:

$$S(t) = S_\infty \left(1 - \exp\left(-\frac{t}{\tau_\sigma}\right)\right)$$

with $\tau_\sigma$ as the retardation constant depending upon the vulcanization coefficient; and the vulcanization coefficient (X) is determined by means of the equation:

$$X = \frac{\ln S_\infty - b}{a}$$

with a and b as constants being derived from the determination of the known vulcanization coefficient of at least two comparison specimens with $S_\infty$ values determined in accordance with the above.

Since this procedure is nondestruction and only requires time in an order of magnitude of ten seconds, it solves the task set.

A preferred application of the procedure being an object of the invention consists in that after the compression of the material specimen, a beam of light is focused onto the relieved surface of the specimen in the selected point, and the focus is made to follow this migrating point; in addition, the recovery distance of this selected point of the specimen surface is measured by following it by means of the focus of the beam of light. In this way, the procedure being the object of the invention can be carried out with relatively simple means with sufficient accuracy, if the diameter of the focal point of the focused beam of light on the selected point of the workpiece is in the order of magnitude of one micrometer. This enables to follow the recovery distance with a precision in the order of magnitude of 0.1 micrometer.

For the preferred application of the procedure being the object of the invention, laser light is used and its parallel beam of light is spread, collimated and focused; furthermore the light reflected from the followed point of the specimen surface is reflected from the path of light and represented in such a way that an enlargement of the spot of light on the followed point of the specimen is converted into a lateral displacement of the represented spot of light; furthermore this displacement is measured and the focussing corrected accordingly. Consequently this constitutes a control for the continuous maintenance of the focussing, with a measurement characteristic, i.e. a dissolving power, which, depending on the reflection capacity of the followed point of the specimen surface is situated between about 2 micrometers for reflecting surfaces and 50 micrometers for faintly reflecting surfaces, as, for example, in the case of heavily scattering (rought) or absorbent (black) surfaces.

The invention is also based on the task of providing an apparatus for the execution of the procedure being the object of the invention.

This task is solved by the component items succeeding each other in the direct path of light, namely: a laser; an optical system for spreading the beam, a collimator; a transparent beam deflector mirror-coated on its reverse side and arranged in an inclined position; an objective as a sensitive member of a control loop; a carrier for the material specimen/finished part and by the component items succeeding each other in the rectangular path of light, namely: a light-spot mapping element 36; a prism; two optoelectronic sensors arranged beside each other; an electronic arrangement as a controller for comparing the sensor output signals and controlling the readjustment of the objective; an electromechanic readjustment device for the objective as an actuator in the control loop of the aforementioned components: objective/light-spot mapping element/prism/sensors/comparison and control arrangement/objective readjustment device/objective; and an electronic system for the application of an equation.

A preferred version of the apparatus being the object of the invention features an adjusting device, a compressing device, a measuring device with the components: laser/light spreading optical system/collimator/beam/deflector/objective/light-spot mapping element/prism/sensors/possibly comparison and control arrangement/objective readjustment device, and a separate electronic evaluation unit with the electronic application system.

In the preferred version the carrier for the material specimen/the finished part is provided as a slide, which can be moved past the compressing device, between the adjusting and the measuring device, either on a straight line or on a circular are which, when extended to a circle, enables the simultaneous setup and the execution of the invention-conform procedure. In the preferred version the measuring device for the rough adjustment of the objective is, as a whole, arranged to be adjustable in relation to the carrier.

Instead of the preferred version of the invention-conform procedure (claim 1), it is possible to use the "triangulation method" mentioned in the magazine "Werkstoffe in der Fertigung 1-2/90" (materials in production) in the essay "Optische Entfernungsmessung mit Laser/Optoelektronik in der dimensionalen MeBtechnik" (optical distance measurement with laser/optoelectronic systems in the dimensional measuring technique) as a prior art method.

Figure 1:
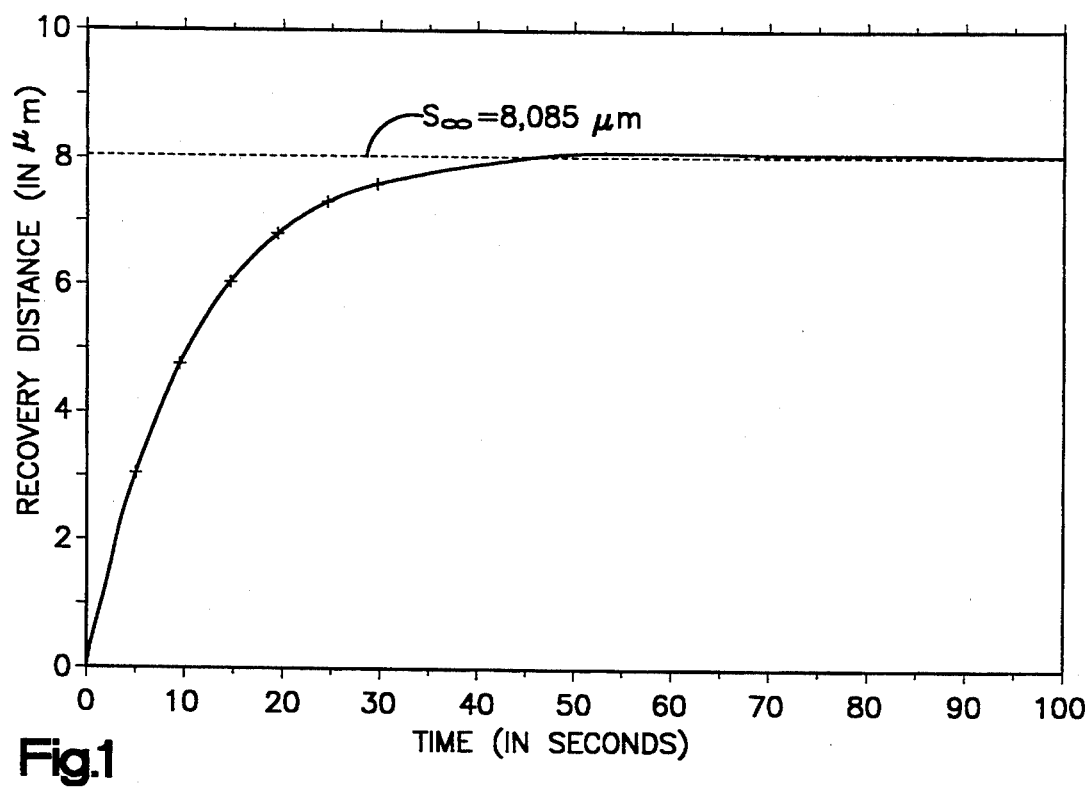
FIG. 1 is a graph schematically showing concepts and relationships in the method of the present invention.

In the following, the invention is explained in detail by means of the preferred version of the invention-conform apparatus for the application of the invention-conform procedure for the determination of the vulcanization coefficient of elastomers illustrated as an example in the drawing.

Figure 2:
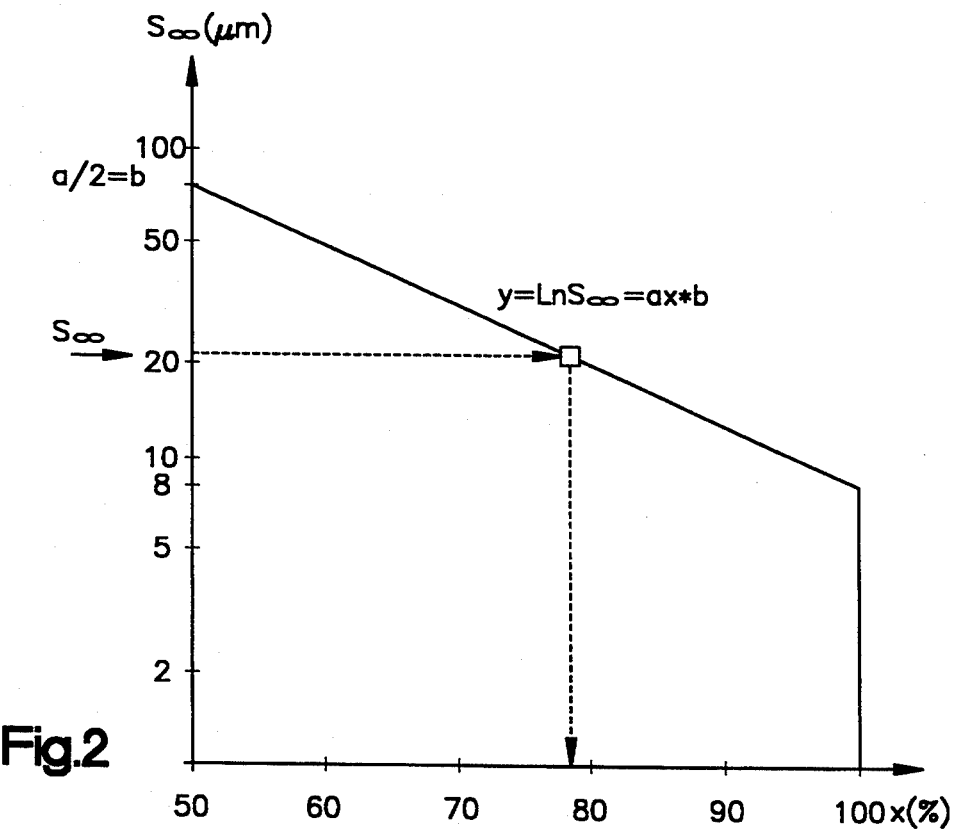
FIG. 2 is a graph schematically showing concepts and relationships in the method of the present invention.

If, on a specimen of the material NBR, vulcanized to 99.9%, after its compression, the recovery or retardation distance S(t) of the relieved specimen surface is measured every five seconds, this results within a time t=30 seconds in six value pairs which are marked by crosses in FIG. 1 and through which a curve is drawn which is extrapolated beyond the time of 30 seconds after the beginning of the measurement, the represented asymptote of which has a value of $S_\infty = 8.085$, the retardation constant $\tau$ is $\tau = 11.079$s. This point-by-point measurement of the recovery distance covered during the retardation of the selected point of the relieved specimen surface as a function of time is carried out so long till the asymptotic value of the retardation distance for an infinitely long measuring time $S_\infty$ can be determined graphically or by calculation. This determination is made graphically and/or by calculation using the equation:

$$S(t) = S_\infty \left(1 - \exp\left(-\frac{t}{\tau_\sigma}\right)\right)$$

with $\tau_\sigma$ as the retardation constant $T_\sigma$ being dependent upon the vulcanization coefficient and automatically obtained during the calculation. For the graphic or calculatory determination of the desired vulcanization coefficient X=0.9999 by using the equation:

$$X = \frac{\ln S_\infty - b}{a}$$

it is necessary to first define the straight line $\ln S_\infty = aX + b$, and this after the determination of the vulcanization coefficient of at least two comparison specimens, the asymptotic values $S_\infty$ of which were determined as shown. This leads to the equation constants a (inclination) and b (point of intersection of the ordinates). After the formation of the natural logarithm of the asymptotic value $S_\infty$ it is possible to read off or calculate the respective value of the desired vulcanization coefficient. FIG. 2 shows a reading example. Compressing and maintenance of the pressure last several seconds or several ten seconds depending upon the elasticity of the workpiece.

Figure 3:
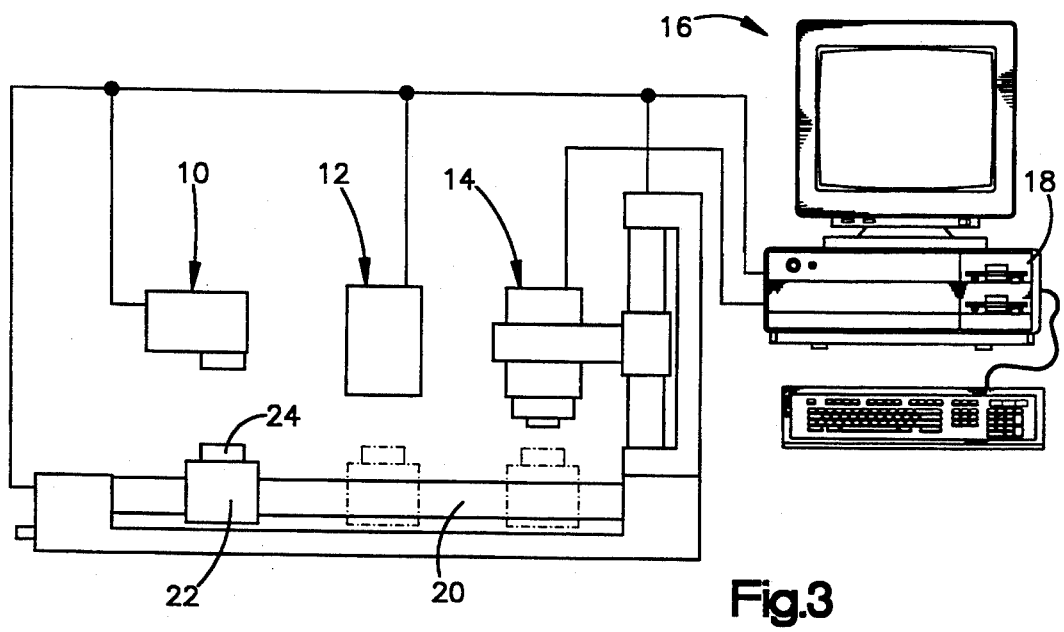
FIG. 3 is a schematic illustration of the apparatus of the present invention.

According to FIG. 3 the invention-conform apparatus of the example consists of an adjusting device 10, a compressing device 12, a measuring device 14, and a separate electronic evaluation unit 16 with application electronic system 18. The three devices 10, 12 and 14 are arranged in a straight line above a straight guide rail 20, on which a slide 22 moves which serves as carrier of a workpiece 24 being a material specimen of a finished part or the finished part itself. That workpiece 24 which can be moved by means of the portable slide 22 is adjusted in the adjusting device 10 in such a way that the surface normal of a selected point of the specimen surface to be loaded is vertical. Thereafter the specimen surface of the workpiece 24 is compressed and held under pressure for a certain setting time by means of the compressing device and then suddenly relieved.

Figure 4:
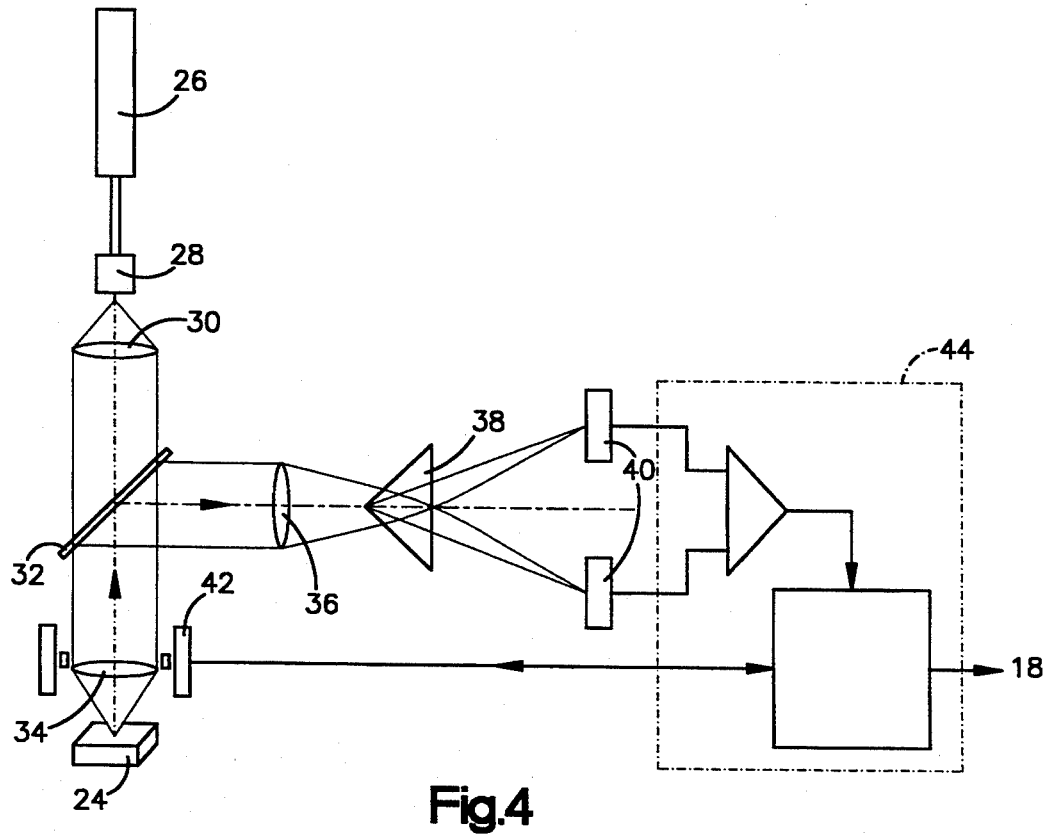
FIG. 4 is a schmematic illustration of the measuring device of the apparatus of the present invention.

The apparatus of the present invention, as shown in FIG. 4, includes items for applying the methods described. These items include a laser 26 and an optical system 28 for spreading the laser beam. Also included are a collimator 30 and a transparent beam deflector 32 mirror coated on the reverse side and mounted in an inclined position. An objective 34 is provided as a sensing or sensitive member of a control loop. A carrier slide 22 carries the material or specimen part 24. Each of these items is in the direct path of light.

In the rectangular or reflected light path a light-spot mapping element 36 is provided followed by a prism 38. This splits the reflected laser beam into two beams which are received by two optoelectronic sensors 40 arranged beside each other. An electronic controller and comparator 44 is connected to receive the output signals of the sensors 40 and compare these signals for controlling the readjustment of the objective 42. The objective 42 serves as an electromechanical readjustment device in the control loop of components based on the compared signals from the sensors 40. The control loop includes the objective 42, the light spot mapping element 36, the prism 38, the sensors 40, the controller and comparator 44, returning to the objective 42.

This allows determination of the coefficient of vulcanization using the formulas described above as calculated by the electronic evaluation unit or computer 16. This, in turn, allows a determination of the degree of vulcanization of the specimen material, whether the actual part or a separate sample.

What is claimed is:

1. A method of determining vulcanization of an elastomeric part comprising the steps of:
    determining the vulcanization coefficient of a principally plane-parallel, elastomeric material specimen of the elastomeric part by
    (a) compressing a surface of the specimen and suddenly relieving the compressed surface,
    (b) measuring the retardation of the relieved surface wherein the recovery distance (S) covered by a selected point of the relieved specimen surface during the retardation, as a function of time (t), is measured until the asymptotic value ($S_\infty$) of the retardation distance (S) can be determined for an infinitely long measuring time;

this asymptotic value ($S^0_\infty$) is determined by means of the equation:

$$S(t) = S_\infty \left(1 - \exp\left(-\frac{t}{\tau_\sigma}\right)\right)$$

with $\tau_{94}$ as the retardation constant depending upon the coefficient of vulcanization; and the coefficient of vulcanization (X) is determined by means of the equation:

$$X = \frac{\ln S_\infty - b}{a}$$

with a and b as constants being derived from the determination of the known vulcanization coefficients of at least two comparison specimens with $S_\infty$ values determined according to the above equation; and determining the extent of vulcanization of the part based on the determined vulcanization coefficient.

2. A method according to claim 1 characterized in that after the compression of the material specimen, a beam of light is focused onto the relieved specimen surface in a selected point and the focus is made to follow the selected point; and in that the recovery distance of the selected point of the specimen surface is measured by following it by means of the focus of the beam.

3. A method according to claim 2 characterized in that laser light is used and its parallel beam is spread, collimated and focused; in that light reflected from the selected point of the specimen surface is reflected from the path of the light beam and represented in such a way that an enlargement of the spot of light on the selected point of the specimen surface is converted into a lateral displacement of the represented spot of light; and in that the lateral displacement is measured and the focusing adjusted accordingly.

4. An apparatus for determining the vulcanization coefficient of a principally plane-parallel, elastomeric material, comprising the following component items succeeding each other in the direct path of light, namely:

a laser for emitting a laser beam;

an optical system disposed for spreading the laser beam;

a collimator disposed for collimating the laser beam after it has passed through the optical system;

a transparent beam deflector mirror-coated on the reverse side and mounted in an inclined position for allowing light from the collimator to pass therethrough while deflecting light reflected from said material;

an objective lens movable to maintain focus on a selected point of the elastomeric material as it moves following a suddenly relieved compression;

a carrier slide for holding material specimen to receive focused light from the objective lens and reflect it through the objective lens to the beam deflector;

a light-spot mapping element to receive reflected light from the beam deflector;

a prism 38 for splitting the beam from the light spot mapping element into two beams;

two optoelectronic sensors arranged beside each other so that each receives one of the two beams from the prism and produces an electrical signal proportional to the beam so received;

an electronic arrangement which receives the electrical signals from the sensors and proportionally control the readjustment of the objective to maintain focus on the material specimen selected point;

an electromechanic readjustment device for moving the objective lens responsive to the electronic arrangement;

an electrical computing device connected to the electronic arrangement and which computes a vulcanization coefficient according to a formula where the recovery distance (S) covered by a selected point of the relieved specimen surface during the retardation, as a function of time (t), is measured so long till the asymptotic value ($S_\infty$) of the retardation distance (S) can be determined for an infinitely long measuring time;

this asymptotic value ($S^0_\infty$) is determined by means of the equation:

$$S(t) = S_\infty \left(1 - \exp\left(-\frac{t}{\tau_\sigma}\right)\right)$$

with $\tau_\sigma$ as the retardation constant depending upon the coefficient of vulcanization; and the coefficient of vulcanization (X) is determined by means of the equation:

$$X = \frac{\ln S_\infty - b}{a}$$

with a and b as constants being derived from the determination of the known vulcanization coefficients of at least two comparison specimens with $S_\infty$ values determined according to the above equation.

5. An apparatus according to claim 4 which further comprises:

a means for compressing and suddenly relieving the selected point of the material specimen.

* * * * *